United States Patent [19]

Bosselaar et al.

[11] 4,123,847
[45] Nov. 7, 1978

[54] APPARATUS FOR MEASURING INTERNAL CORROSION IN PIPELINES

[75] Inventors: Hendrik Bosselaar; Frank Oltmans, both of Amsterdam, Netherlands

[73] Assignee: Shell Oil Company, Houston, Tex.

[21] Appl. No.: 841,631

[22] Filed: Oct. 13, 1977

[30] Foreign Application Priority Data

Oct. 22, 1976 [NL] Netherlands .......................... 7611703

[51] Int. Cl.² ............................ G01B 7/12; G01B 7/34
[52] U.S. Cl. .................................. 33/178 E; 33/178 F; 33/DIG. 13
[58] Field of Search ......... 33/178 E, 178 F, DIG. 13; 73/152

[56] References Cited

U.S. PATENT DOCUMENTS

| 2,398,562 | 4/1946 | Russell | 33/178 F |
|---|---|---|---|
| 2,497,990 | 2/1950 | Huber et al. | 33/178 F |
| 2,607,128 | 8/1952 | Newhall | 33/178 E |
| 2,854,758 | 10/1958 | Owen | 33/178 F |
| 2,896,332 | 7/1959 | Elston et al. | 33/178 F |
| 3,024,651 | 3/1962 | McGlasson | 33/178 F |
| 3,882,606 | 5/1975 | Kaenel et al. | 33/174 L |
| 3,898,741 | 8/1975 | Casey | 33/178 F |

FOREIGN PATENT DOCUMENTS 512,091  8/1939  United Kingdom ................. 33/178 E

*Primary Examiner*—Richard R. Stearns

[57] ABSTRACT

An apparatus for measuring the internal corrosion in a pipeline consisting of a pig having a circumferential array of spring-loaded probes for measuring both the average diameter of the pipe and the depth of individual pits. The probes are disposed in pairs with one probe in the form of a stylus having a pointed end for measuring pits, and the other probe having a shoe-shaped end for measuring the average pipe diameter.

3 Claims, 3 Drawing Figures

APPARATUS FOR MEASURING INTERNAL CORROSION IN PIPELINES

BACKGROUND OF THE INVENTION

The invention relates to an apparatus for measuring internal dimensions or corrosion of a pipeline.

The steel wall of a pipeline may be subject to internal corrosion depending, obviously, on the matter that is transported through the pipeline. Both liquids and gases may attack the steel wall and produce two forms of corrosion; namely, uniform corrosion and pitting. In the case of uniform corrosion, the wall thickness decreases more or less uniformly, and it will be clear that this will eventually lead to the pipeline becoming unserviceable, because the wall will become too weak to resist the internal pressure. Pitting leads to leakage, and this phenomenon must also be avoided. It is, obviously, of great importance to constantly know the state of the pipeline to be able to take corrective action in time.

Since downtime is costly, it is preferred that the inspection of pipelines be carried out while they are in operation. Moreover, pipelines are often installed where access is difficult, e.g. underground or underwater, so that methods of internal inspection are preferred.

U.S. Pat. No. 2,896,332 discloses an apparatus for inspecting the interior of a pipeline comprising a pig carried along by the flow of matter through the pipeline. The pig is fitted with a circular array of spring-loaded probes protruding radially outwards, and pressed against the inner wall of the pipeline. The probes are fitted with displacement pickups, and the pig is equipped with apparatus for processing the signals from the displacement pickups and recording the results of such processing. The pig is further fitted with means for the determination of the distance traveled by the pig. This may be a time clock whose signal is regularly recorded and may be used in conjunction with the pumping schedule to determine the location of the pig at any time. It is also possible to use a supporting wheel whose revolutions indicate the location of the pig.

BRIEF SUMMARY OF THE INVENTION

It is of the utmost importance to have an apparatus by which both uniform corrosion and pitting can be determined quantitatively, and the invention indicates the means by which this can be achieved.

The invention therefore relates to an apparatus of the type described hereinbefore in which the probes are arranged in pairs; one probe having a stylus or pointed shape and the other a shoe shape. Each of the probes can move independently of the other in a radial direction with the extremities of each pair being near to each other. The two probes of a pair are spring-connected with the body of the pig and with each other; and one displacement pickup is located between the body of the pig and the stylus-shaped probe, and one displacement pickup is located between the shoe-shaped and the stylus-shaped probe.

A shoe-shaped probe responds to uniform corrosion and not to pitting because of its size, while the stylus-shaped probe responds to both forms of corrosion. When a pit is located in an area already attacked by uniform corrosion, the deflection of the stylus-shaped probe is misleading as regards the depth of the pit. This probe indicates too great a depth here, but deducting the deflection of the shoe-shaped probe from that of the stylus-shaped probe, the actual depth of the pit is found.

This is possible because there are two displacement pickups, as indicated. In addition to the pit depth, the uniform corrosion is also measured. It is important that the extremities of the two probes are in each other's proximity since all sorts of irregularities may occur in the wall of the pipeline, which may lead to inaccurate results. Very reliable results are obtained with an apparatus in which the shoe-shaped probe has a hole in the part that lies against the wall of the pipeline, through which hole the stylus-shaped probe can move freely in a radial direction. This design will enable both forms of corrosion, if present at the same location, to be measured individually. To reduce the possibility that an irregularity on the wall at some distance from a pit may disturb the shoe-shaped probe, it is desirable for the geometry of the shoe-shaped probe to be such that there is no more than about line contact with the wall of the pipeline. The hole for the stylus-shaped probe is located in this line. In comparison with a sole- or slide-shaped probe, this design greatly reduces the risk of the shoe being forced back by an irregularity when the stylus-shaped probe measures a pit. Irregularities regularly encountered are, for example, weld reinforcements.

The independently movable probes of a pair should preferably be assembled with the aid of approximately leaf spring devices, the first spring device connecting the stylus-shaped probe near its protruding tip to the inner surface of the shoe-shaped probe, the second spring device connecting the inner end of the stylus-shaped probe to the body of the pig, the third spring device connecting the stylus-shaped probe at a point intermediate it's end to the shoe-shaped probe, and the fourth spring device connecting the shoe-shaped probe at about the same point to the body of the pig. This assembly determines the position and provides the free movement of the stylus-shaped probe relative to the shoe-shaped probe and conversely, which is especially important when the stylus-shaped probe passes through a hole in the shoe-shaped one.

The displacement pickups, preferably consisting of flat springs fitted with strain gauges, are disposed to measure the movement of the two probes. Good results are obtained when the first measuring spring is located below the second spring device; one end of the measuring spring being clamped to the body of the pig while the other end is forced against the inner end of the stylus-shaped probe. When the second measuring spring is located between the second and third spring device, one end of the measuring spring being clamped to the shoe-shaped probe, the other end is also forced against the intermediate point on the stylus-shaped probe. This assembly provides an accurate measurement of the displacement of the stylus-shaped probe and its displacement relative to the shoe-shaped probe, as well as an accurate measurement of the displacement of the shoe-shaped probe.

There may be, for instance, twelve pairs of probes placed in a circular array of diametrically opposite pairs around the pig. Thus, six diameters can be measured in a cross-section of the pipeline. Measurements may be started immediately after commissioning of the pipeline to provide a base record that will yield data such as out-of-roundness, constrictions, location and size of weld reinforcements, joints, et cetera. These data are important for a correct interpretation of subsequent measurements.

BRIEF DESCRIPTION OF THE DRAWINGS

The invention will now be further elucidated with reference to some figures.

PREFERRED EMBODIMENT

Figure 1:
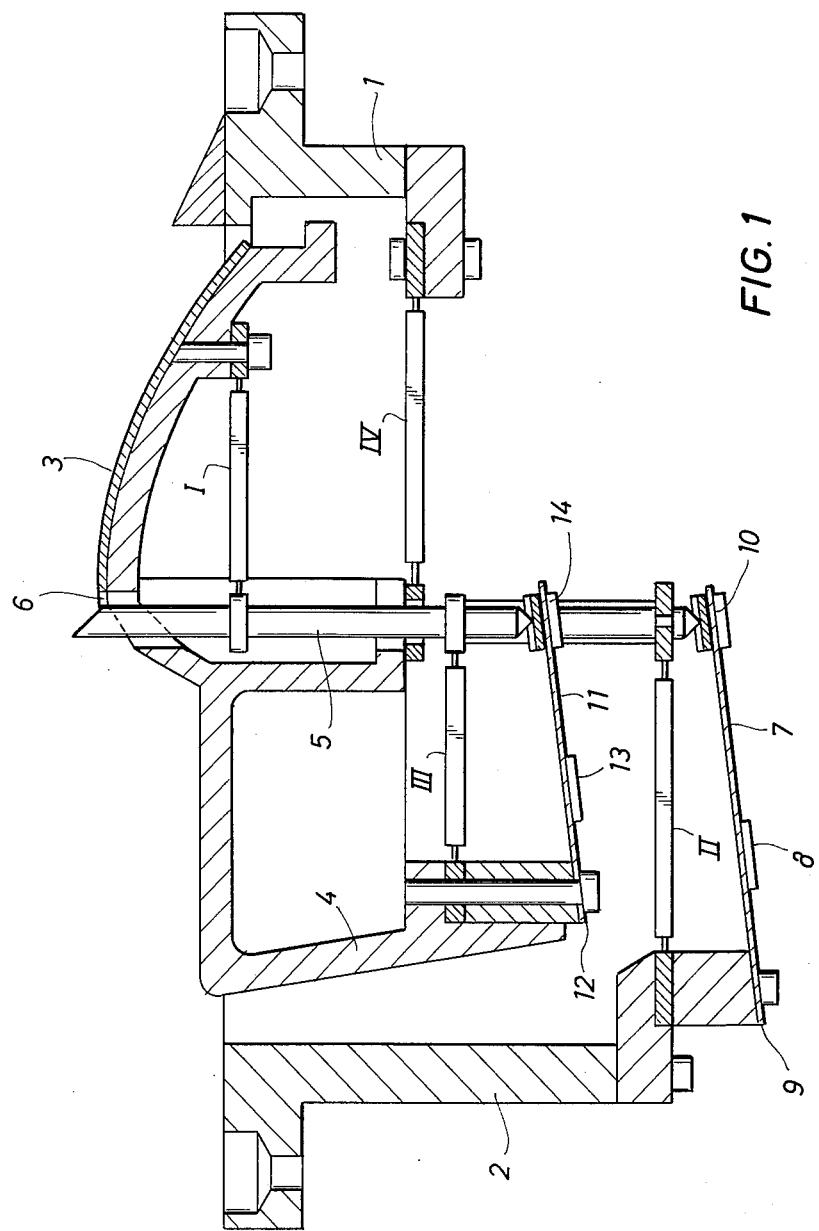
FIG. 1 shows a pair of probes belonging together.
Figure 2:
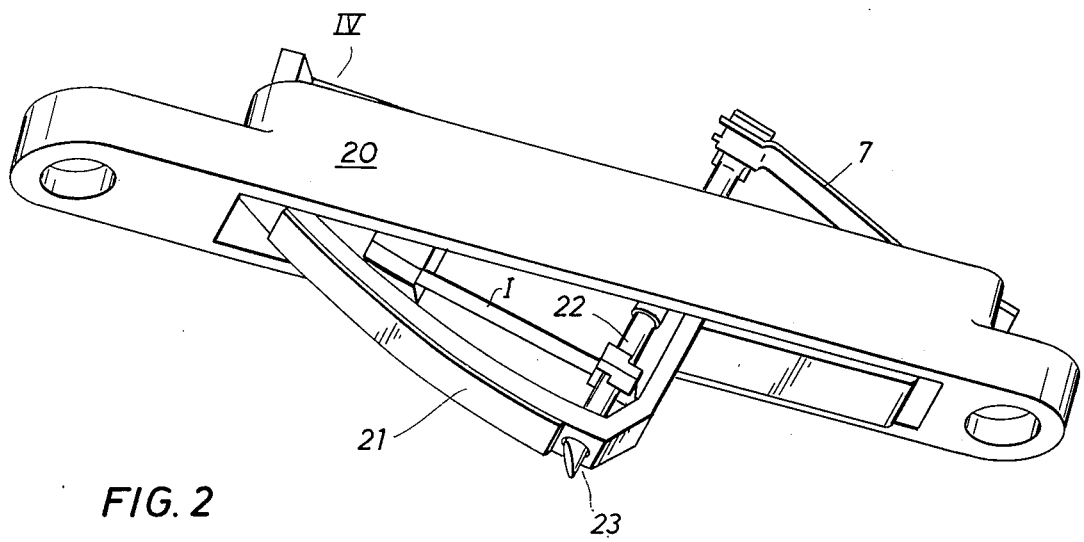
FIG. 2 shows an assembly of such a pair in a housing.

In FIG. 1, 1 and 2 represent part of the body of the pig, rigidly interconnected by other parts not shown here. A shoe-shaped probe is represented by 3, which probe is integral with the probe body 4. A stylus-shaped probe 5 can move freely in its longitudinal direction through opening 6 in the shoe-shaped probe 3. This direction corresponds with a radial direction of the pipeline when the pig is placed in it.

A system of four spring devices, indicated by Roman numerals I-IV, ensures that the positions of the two probes are maintained, and that the probes exert sufficient pressure on the pipewall. Spring devices I and III determine the position of the tip of probe 5 in opening 6 of probe 3. Spring device IV exerts the outward force on shoe-shaped probe 3, spring device II does the same on stylus-shaped probe 5. The spring devices have been drawn here as leaf springs. By changing the points of application, spring device IV, for instance, may be constructed as a powerful helical spring.

Spring 7 is the first measuring spring, fitted with strain gauge 8 and is clamped to the body 2 at one end 9 while other end 10 follows the movement of probe 5. Spring 11 is the second measuring spring, which is clamped at 12 to securing part 4 of shoe-shaped probe 3. On this spring, a strain gauge 13 is mounted, and end 14 again follows the movements of probe 5, but now relative to the position of shoe-shaped probe 3.

FIG. 2 shows an embodiment of a pair of probes wherein the housing 20 may be firmly connected to the body of the pig. Controlled by spring devices, the shoe-shaped probe 21 and the stylus-shaped probe 22 can move freely within this housing. Tip 23 of probe 22 projects outwards through an opening in shoe 21. Some spring devices are visible, in particular, spring device I of FIG. 1, and a small part of spring device IV, which here is constructed as a helical spring. The first measuring spring 7 is also visible.

Figure 3:
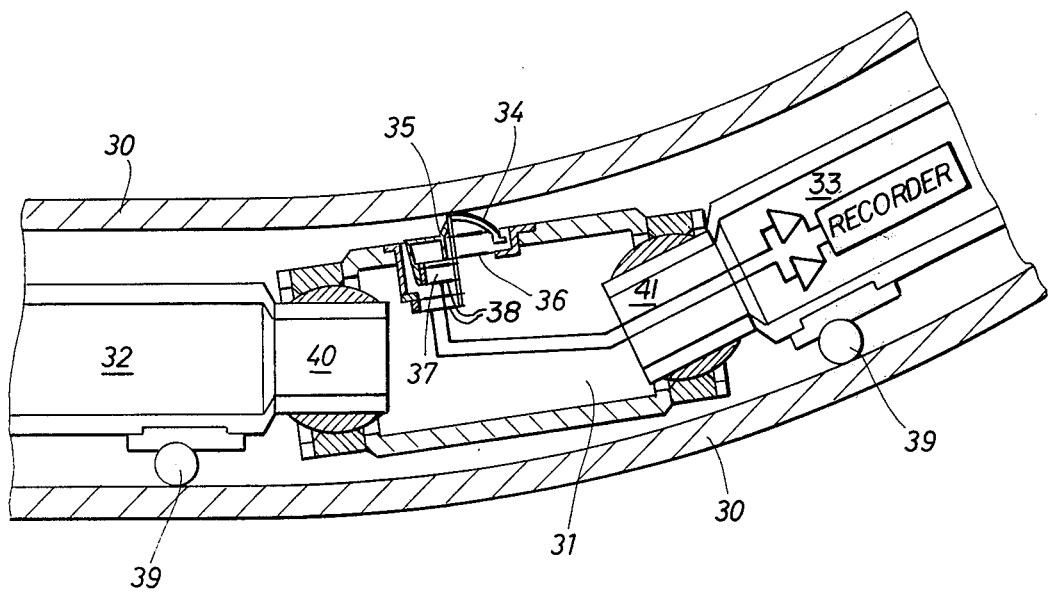
FIG. 3 shows a pig with a number of joints.

As shown in FIG. 3, the circular array of probes is preferably accommodated in an open section of the pig, which open section is connected by ball joints 40 and 41, to at least two closed sections—fitted with supporting wheels—viz. at least one closed section on either side of the open section. The wall of the pipeline is indicated by 30, the open section by 31, the closed sections, at least partly, by 32 and 33. Shoe-shaped probe 34 and stylus-shaped probe 35 are connected with the open body 31 by means of spring systems 36 and 37. Only one pair of probes is shown here. The measuring springs are indicated by 38.

Supporting wheels 39, of which only two are drawn, carry the pig while the ball joints 40 and 41 allow movements of the sections relative to each other. The medium in the pipeline—e.g. oil or gas—can penetrate into section 31, but is kept out of sections 32 and 33 by seals in ball joints 40 and 41. Section 32 may, for instance, contain the batteries for feeding the data processing and recording equipment, which equipment may be located in section 33. The pig may be extended to include a fourth section, to which may be attached the measuring wheel for the determination of distance. Entrainment of the medium may be effected by one or more collars lying against the wall, e.g. attached to a pulling device.

The signals originating from the strain gauges may be processed using standard elements, such as amplifiers, adders and subtracters, to yield the desired information. Data recording may be done by means of a magnetic tape, but other memories from which information can be read may be used as well.

The speed at which the pig moves through the pipeline depends on the pumping rate and may be up to 10 m/s. The variation in pipeline diameter may be between 0-30 mm, the accuracy of measurement is about 1 mm. Pits can also be measured with an accuracy of 1 mm. The shoe-shaped probe can follow a maximum frequency of about 40 Hz, the stylus-shaped probe about 120 Hz.

What is claimed is:

1. An apparatus for measuring both the average internal diameter of a pipeline and the depth of the individual pits, said apparatus comprising:
   a pipeline pig having at least one open section;
   a plurality of pairs of probes disposed around the periphery of said open section, each pair of probes having a shoe-shaped probe and a pointed-end probe disposed to project through an opening in the pipeline contacting surface of the shoe-shaped probe;
   a plurality of flat spring members disposed to support said probes both with respect to each other and said open section, said probes moving relative to each other in a radial direction;
   a plurality of strain gauges mounted on said flat spring members to measure the deflection of said spring members; and,
   a recording means carried by said pig and coupled to said strain gauges to record the deflection of said spring members.

2. The apparatus of claim 1 wherein said pointed-end probe is supported adjacent its pointed end by a first flat spring member disposed between the probe and said shoe-shaped probe, said pointed-end probe being supported adjacent its other end by a second flat spring member disposed between the pointed-end probe and said pig, said pointed-end probe being supported at an intermediate position by a third flat spring member disposed between the pointed-end probe and the shoe-shaped probe, and said shoe-shaped probe being supported adjacent the intermediate position on said pointed-end probe by a fourth flat spring member disposed between said shoe-shaped probe and said pig.

3. The apparatus of claim 1 wherein a fifth flat spring member is disposed below said second spring member, and having one end clamped to the pig to force the other end into contact with said pointed-end probe, a sixth flat spring member disposed between said second and third spring members, and having one end clamped to the shoe-shaped probe to force the other end into contact with said pointed-end probe; and a pair of strain gauges, one of said strain gauges being mounted on each of said fifth and sixth flat spring members to measure the deflection thereof.

* * * * *